United States Patent [19]

Sakagami

[11] Patent Number: 4,849,176
[45] Date of Patent: Jul. 18, 1989

[54] AUTOMATIC SAMPLE DELIVERY APPARATUS FOR USE IN AUTOMATIC CHEMICAL ANALYZER

[75] Inventor: Toshio Sakagami, Chofu, Japan

[73] Assignee: Olympus Optical Co., Ltd., Tokyo, Japan

[21] Appl. No.: 52,876

[22] Filed: May 22, 1987

[30] Foreign Application Priority Data

May 28, 1986 [JP] Japan .................. 61-122882

[51] Int. Cl.$^4$ .......................... G01N 35/04
[52] U.S. Cl. ........................ 422/64; 422/65
[58] Field of Search ................... 422/64, 65

[56] References Cited

U.S. PATENT DOCUMENTS

| 4,260,580 | 4/1981 | Sindo et al. ............ 422/64 |
| 4,268,477 | 5/1981 | Herzstark ............... 422/64 |
| 4,276,051 | 6/1981 | Ginsberg et al. . |
| 4,528,159 | 6/1985 | Liston ................... 422/64 |
| 4,595,562 | 6/1986 | Liston et al. ........... 422/64 |
| 4,668,617 | 5/1987 | Furuta et al. .......... 422/64 |
| 4,713,974 | 12/1987 | Stone ................... 422/64 |

FOREIGN PATENT DOCUMENTS 0035320 9/1981 European Pat. Off. .
2733074 2/1979 Fed. Rep. of Germany .
3306491 9/1983 Fed. Rep. of Germany .

Primary Examiner—Michael S. Marcus
Assistant Examiner—D. John Griffith, Jr.
Attorney, Agent, or Firm—Arnold, White & Durkee

[57] ABSTRACT

An automatic sample delivery apparatus for delivering selectively emergency samples and standard samples by interrupting the delivery of successive routine samples, including a main-turntable on which a plurality of emergency and standard sample vessel holding recesses are formed equidistantly along a first circle, a plurality of sub-turntables arranged rotatably on the main-turntable, each having a plurality of routine sample vessel holding recesses formed equidistantly along a second circle, a main-motor for rotating the main-turntable such that any one of the sub-turntables is indexed into a sample delivery position and any one of the emergency and standard sample holding recesses is indexed into a sample sucking position, and a sub-motor for rotating a sub-turntable indexed into the sample delivery position such that routine samples set on the relevant sub-turntable are indexed into the sample sucking position. Any of the routine, emergency and standard samples indexed into the sample sucking position is delivered into a reaction vessel by the same sample sucking device in the same manner.

6 Claims, 2 Drawing Sheets

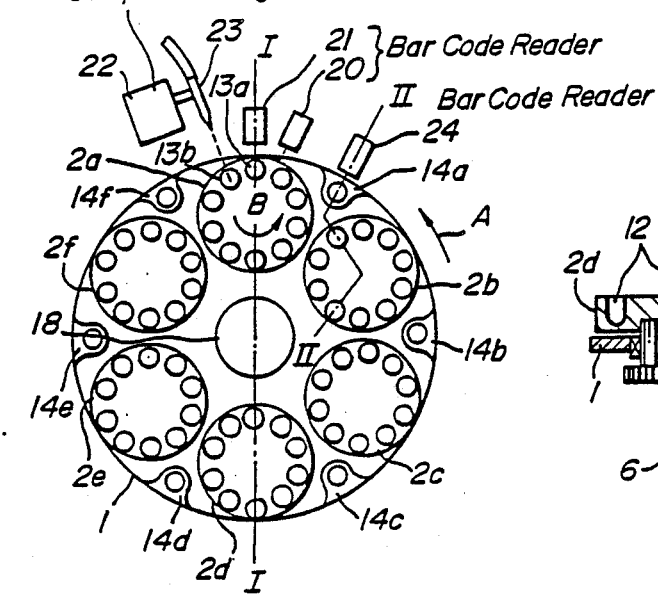
FIG_1
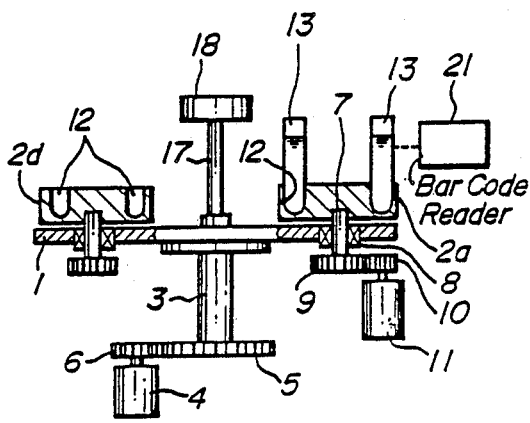
FIG_2
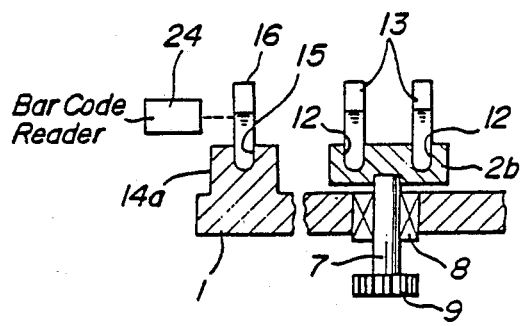
FIG_3

AUTOMATIC SAMPLE DELIVERY APPARATUS FOR USE IN AUTOMATIC CHEMICAL ANALYZER

BACKGROUND OF THE INVENTION

This invention relates to an automatic sample delivery apparatus for use in an automatic chemical analyzer in which one or more emergency samples and standard samples can be predominantly delivered by interrupting the delivery of successive routine samples.

Various types of automatic chemical analyzers have been used for automatically analyzing and testing components contained in various samples, such as serum and urine samples. In general, samples to be analyzed are contained in sample vessels or tubes which are set in an automatic sample delivery apparatus, usually called a sampler. In the sampler the sample vessels are fed along a given path through a sample sucking position at which a given amount of a sample contained in a sample vessel just indexed to the position is sucked into a sucking probe. The sample thus sucked in the probe is delivered or discharged into one or more reaction vessels. In such an automatic chemical analyzer, a number of sample vessels set in the sampler are successively indexed into the sample sucking position, and successive samples are delivered into reaction vessels in a given order. In order to analyze one or more emergency samples and standard samples for effecting the calibration, the emergency samples and standard samples have to be predominantly delivered by interrupting the normal delivery of successive routine samples.

In German Patent Application Laid-Open Publication (Offenlegungschrift) No. 33 06 491 there is disclosed an automatic chemical analyzer in which an emergency sample holder is swingably arranged above the feeding path of the routine samples at the sample sucking position and, when an emergency sample is to be analyzed, a sample vessel containing the emergency sample is set in the holder and the holder is swung into a position which is aligned with the sample sucking position. In such an apparatus, since the emergency sample is set at a level above the feeding path of routine samples, the emergency sample could not be identified by a device for identifying the routine samples, so that the emergency sample might not be accurately identified. Therefore, test results of the emergency samples and standard samples might not be clearly distinguished from each other as well as from those of the routine samples. Further, the sample sucking probe has to pick up samples both at the lower routine sample sucking position and at the upper emergency sample sucking position, and therefore the probe must move over a long distance. As a result, the sample sucking device, including the probe and its driving mechanism, becomes large in size and complicated in construction. Further, the sample delivery precision is liable to be unacceptable.

In European Patent Application Publication No. 0035320 and U.S. Pat. No. 4,276,051, there are described automatic chemical analyzers in which routine samples are set along outer circles on a turntable and emergency and standard samples are set along the innermost circle on the turntable. A sample sucking probe is arranged movably over substantially a radius of the turntable so that an emergency sample can be sucked into the probe. Also, in such an analyzer ID marks such as bar codes provided on the emergency sample vessels could not be read out by the same ID reading device for reading ID marks on the routine sample vessels. Further, since the sucking probe has to move over a relatively long path above the turntable, the sample sucking device is liable to be large and complicated. Moreover, during the delivery of the emergency samples, the emergency samples sucked into the probe might drop into routine sample vessels to cause contamination. Such contamination of samples results in serious errors of measurement.

SUMMARY OF THE INVENTION

The present invention has for its object provision of an automatic sample delivery apparatus which can mitigate the above mentioned drawbacks of the known sample delivery apparatuses and can deliver emergency and standard samples by indexing them into substantially the same sample sucking position as that for routine samples.

It is another object of the invention to provide an automatic sample delivery apparatus in which the emergency and standard samples can be correctly distinguished from the routine samples, while the emergency and standard samples are identified by the same device for identifying the routine samples.

According to the invention, an automatic sample delivery apparatus, for automatically delivering routine samples contained in routine sample vessels and special samples such as emergency samples and standard samples contained in special sample vessels to be analyzed by an automatic chemical analyzer, comprises a first sample holding means for supporting routine sample vessels and feeding the routine sample vessels along a first path;

a second sample holding means for supporting special sample vessels and feeding the special sample vessels along a second path which is arranged substantially at the same level as said first path and includes a portion substantially coincident with a portion of said first path at least at a sample sucking position; and a sample sucking device including a sucking probe for sucking routine samples and special samples indexed into said sample sucking position.

BRIEF DESCRIPTION OF THE DRAWINGS

FIG. 1 is a schematic plan view showing an embodiment of the automatic sample delivery apparatus according to the invention;

FIG. 2 is a cross sectional view of the apparatus cut along a line I—I in FIG. 1;

FIG. 3 is a cross sectional view of the apparatus cut along a line II—II in FIG. 1.

DESCRIPTION OF THE PREFERRED EMBODIMENTS

Figure 4:
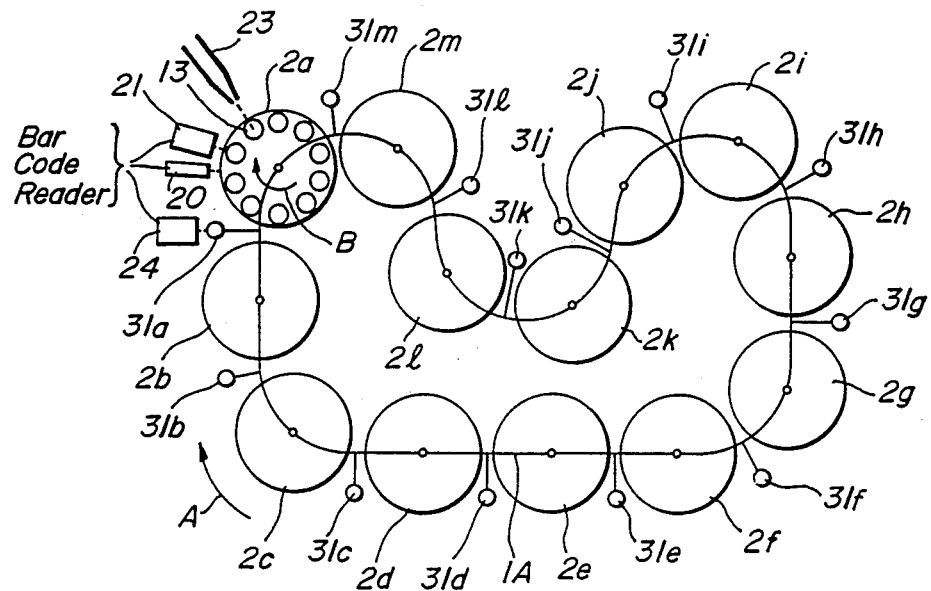
FIG. 4 is a schematic plan view depicting another embodiment of the automatic sample delivery apparatus according to the invention.

FIGS. 1 to 3 show an embodiment of the automatic sample delivery apparatus according to the invention. In this embodiment, the apparatus comprises a main-turntable 1 and a plurality of sub-turntables $2a \sim 2f$. The six sub-turntables $2a \sim 2f$ are equidistantly arranged on the main-turntable 1 along a circumference thereof. The main-turntable 1 is rotatably supported by a main-shaft 3 which is coupled with a main-motor 4 via gears 5 and 6. Therefore, by driving the main-motor 4, the main-turntable 1 is rotated in a direction shown by an arrow A in FIG. 1. As will be explained later, the main-turntable 1 is rotated intermittently by a unit angle of 60° (=360°/6). To the sub-turntables 2 are secured sub-shafts 7, respectively, which are rotatably journaled by bearings 8 provided on the main-turntable 1. To each sub-shaft 7 is connected a respective gear 9. Any one of the gears 9 is selectively engaged with a gear 10 connected to an output shaft of a sub-motor 11 secured to a fixed member. In FIG. 1, the sub-turntable 2a is indexed at a sample delivery position, so that the gear 9 connected to the relevant sub-turntable 2a is engaged with the gear 10 as illustrated in FIG. 2. Then, by driving the sub-motor 11, the sub-turntable 2a indexed at the sample delivery position is rotated in a direction shown by an arrow B in FIG. 1. As will be explained later, the sub-turntable 2a is rotated intermittently over a unit angle of 36° (=360°/10).

Each of the sub-turntables 2a to 2f have formed therein ten recesses 12 for holding sample vessels 13 containing routine samples. These recesses 12 are formed equidistantly along a circumference of the sub-turntable. Therefore, a maximum of sixty sample vessels 13 containing routine samples can be initially set on the sample delivery apparatus.

Along a periphery of the main-turntable 1, there are formed six projections 14a~14f at middle points between successive sub-turntables 2a~2f. In an upper surface of the projection is formed a recess 15 for holding an emergency sample vessel 16 containing an emergency sample or a standard sample. As shown in FIG. 3, each projection 14a~14f has such a height that the emergency sample vessel 16 is situated at the same level as the routine sample vessels 13.

As shown in FIG. 2, a rod 17 is secured to the main-turntable 1 at its center and a disc-shaped handle 18 is connected to a free end of the rod. By grasping the handle 18, the main-turntable 1 with the six sub-turntables 2a~2f can be moved upward. In this manner the turntable assembly can be easily replaced by a new one. To this end, the main-shaft 3 is composed of two shaft portions, one being secured to the main-turntable 1 and the other being secured to the gear 5.

On a peripheral side surface of each of the sub-turntables 2a~2f there is formed a bar code for identifying respective sub-turntables. These sub-turntable identifying bar codes are optically read out by means of a first bar code reader 20 arranged beside the main-turntable 1 as shown in FIG. 1. On an outer surface of each routine sample vessel 13 is also provided a bar code for identifying respective routine samples. These routine sample identifying bar codes are optically read out by a second bar code reader 21 arranged beside the main-turntable 1. In FIG. 1, a routine sample vessel 13a on the sub-turntable 2a is indexed at the sample identifying bar code reading position. Near the second bar code reader 21 there is arranged a sample sucking device 22 having a sucking probe 23. In FIG. 1, for the sake of simplicity, the probe 23 is shown beside the main-turntable 1, but in practice the probe 23 is arranged just above a routine sample vessel 13b on the sub-turntable 2a. Therefore, the position in which the routine sample vessel 13b is situated is called a sample sucking position.

Around the main-turntable 1, there is further provided a third bar code reader 24 which detects optically bar codes provided on the emergency sample vessels 16. It should be noted that the third bar code reader 24 is sufficient for producing a signal representing existence and non-existence of the emergency sample vessels 16, and it is not necessary that it read detailed information about emergency samples.

Now the operation of the automatic sample delivery apparatus of the present embodiment will be explained. At first, the usual operation for delivering successive routine samples will be explained. By driving the main-motor 4, the main-turntable 1 is rotated by 60° so that the sub-turntable 2a is indexed into the sample delivery position. In this position the gear 9 of the relevant sub-turntable 2a is selectively engaged with the gear 10. Then the bar code provided on the sub-turntable 2a is read out by the first bar code reader 20 to identify the relevant sub-turntable 2a. Next, the bar code provided on the sample vessels 13 containing routine samples are successively read out by the second bar code reader 21, while the sub-turntable 2a is intermittently rotated at the step angle of 36° by means of the sub-motor 11. When the identified sample vessel 13b is indexed into the sample sucking position, the probe 23 of the sample sucking device 22 is moved downward into the sample vessel 13b and a predetermined amount of the routine sample contained therein is sucked into the probe 23. Then the probe 23 is moved upward away from the sample vessel 13b. Usually the probe is further moved into a sample discharging position and the sucked routine sample is discharged into a reaction vessel. Since the sample discharging section, reacting section and measuring section of the analyzer are not important for the present invention, these sections are not shown in the drawings, and their explanation is dispensed with.

Next, the sub-turntable 2a is rotated again by 36° and the sample vessel 13a is next indexed into the sample sucking position. Then, a predetermined amount of the routine sample contained in the relevant sample vessel 13a is sucked into the probe 23, and the sucked sample is discharged into a reaction vessel. In this manner, the successive routine samples contained in the sample vessels 13 set on the sub-turntable 2a are delivered into successive reaction vessels, while the sub-turntable 2a is intermittently rotated by 36° with the aid of the sub-motor 11.

After all the routine samples set on the relevant sub-turntable 2a have been delivered, the main-motor 4 is driven again to rotate the main-turntable 1 by 60° so that a next sub-turntable 2b is indexed into the sample delivery position and routine samples set on the relevant sub-turntable 2b are successively delivered by rotating the sub-turntable 2b by means of the sub-motor 11. In this manner, the routine samples contained in the sample vessels 13 set on the sub-turntables 2a~2f can be delivered successively by the sample sucking device 22, while respective routine samples are identified by the bar codes read out by the first and second bar code readers 20 and 21.

When it is required to analyze one or more emergency and standard samples, one or more sample vessels 16 containing the emergency and standard samples are set in the recesses 15 formed in the projections 14a~14f of the main-turntable 1. In the present embodiment, a maximum of six emergency and standard sample vessels 16 can be set on the main-turntable 1 at a time.

When an emergency sample test start switch provided on the apparatus is actuated, the main-turntable 1 is rotated until the emergency sample vessel 16 is detected by the third bar code reader 24. When the bar code reader 24 detects the emergency sample vessel 16, the rotation of the main-turntable 1 is stopped, and then the main-turntable 1 is rotated again by 30° so that the emergency sample vessel 16 is indexed in front of the second bar code reader 21 and a bar code provided on the relevant emergency sample vessel 16 is read out by the reader 21. In this case, the level of the emergency sample vessel 16 is substantially the same as that of the routine sample vessels 13, and the bar codes on these sample vessels 16 and 13 can be accurately read out by the same bar code reader 21. Then, the main-turntable 1 is further rotated by such an angle that the relevant emergency sample vessel 16 is indexed substantially into the sample sucking position.

It should be noted that a radius a circle along which the emergency sample vessels 16 are arranged on the main-turntable 1 is not equal to a radius of a circle along which the routine sample vessels 13 are arranged on the sub-turntables $2a \sim 2f$, so that both the bar code reading position and the sample delivery position for the emergency samples cannot be made coincident with those for the routine samples. In the case of optically reading the bar code provided on the sample vessels, even if a distance from the bar code reader and the bar codes on the sample vessels is slightly changed, the bar codes can be read out accurately. Therefore, in the present embodiment, the circles of the emergency sample array and the routine sample array are crossed with each other at the sample sucking position. When the emergency sample vessel 16 is indexed into the sample sucking position, a predetermined amount of the emergency sample contained therein is sucked into the probe 23 of the sample sucking device 22. It should be noted that the operation of sucking the emergency sample is entirely the same as that of sucking the routine samples, while the emergency sample can be accurately distinguished from the routine samples and the information about the emergency sample can be easily and accurately detected by the second bar code reader 21. Then the emergency sample sucked in the probe 23 is discharged into a reaction vessel.

Then the main-turntable 1 is rotated again until a next emergency sample vessel 16 is detected by the third bar code reader 24. After the next emergency sample vessel 16 has been detected, the main-turntable 1 is once again stopped and is rotated again by 30° and the bar code on the relevant emergency sample vessel 16 is read out by the second bar code reader 21 to detect detailed information about an emergency sample contained in the relevant emergency sample vessel 16. Then, the main-turntable 1 is rotated by the small angle to index the relevant vessel 16 into the sample sucking position. After that the emergency sample contained in the relevant vessel 16 is sucked into the probe and the sucked emergency sample is discharged into a reaction vessel.

The above operation is repeated until all the emergency samples set on the main-turntable are delivered. It should be noted that in the above explanation only the emergency samples are delivered, but the standard samples may be delivered in entirely the same manner. After all the emergency and standard samples have been delivered, the apparatus is returned into the routine sample delivery operation and routine samples are delivered successively in the manner explained above.

FIG. 4 is a schematic plan view showing another embodiment of the automatic sample delivery apparatus according to the invention. In the present embodiment, the main feeding mechanism is constructed by a snake chain 1A. The snake chain 1A is rotated in a direction A by means of a suitable driving mechanism not shown. The snake chain 1A supports thirteen turntables $2a \sim 2m$ and thirteen emergency sample holding members $31a \sim 31m$ which are provided at middle points between successive turntables. The turntables $2a \sim 2m$ are rotatably secured to the snake chain 1A. A turntable $2a$ is in a sample delivery position, and the remaining turntables $2b \sim 2m$ are successively indexed into the sample delivery position by rotating the snake chain 1A in the direction A. At the sample delivery position the turntable $2a$ is selectively engaged with a turntable rotating mechanism not shown. Beside the turntable $2a$ indexed into the sample delivery position there are arranged a first bar code reader 20 for reading the bar codes provided on the turntables, a second bar code reader 21 for reading the bar codes provided on routine and emergency sample vessels, and a third bar code reader 24 for detecting the bar codes on the emergency sample vessels. Further, a sample sucking probe 23 is arranged at a sample sucking position.

The routine sample vessels on the turntables $2a \sim 2m$ and the emergency and standard sample vessels held by the holding members $31a \sim 31m$ are situated at the same level, so that second bar code reader 21 can read the bar codes both on the routine sample vessels and the emergency and standard sample vessels, and both the routine samples and the emergency and standard samples can be delivered by the same sample sucking probe 23 in entirely the same manner at the same sample sucking position. That is to say that by rotating the snake chain 1A, the emergency and standard sample vessels held in the holding members $31a \sim 31m$ are indexed into the same sample sucking position as the routine samples.

The operation of the sample delivery apparatus of the present embodiment is substantially the same as that of the previous embodiment, and thus its detailed explanation is omitted.

As explained above, in the automatic sample delivery apparatus according to the invention the routine samples and the emergency and standard samples are selectively indexed into substantially the same sample sucking position as well as into substantially the same bar code reading position, the routine samples and the emergency and standard samples can be delivered by the same sample sucking device in entirely the same manner, and the bar codes on the routine sample vessels and the emergency and standard sample vessels can be read by the same bar code reader in entirely the same manner. Therefore, the accuracy of the sample delivery can be improved.

Further, the routine samples and the emergency and standard samples are set on the different sample feeding devices, the emergency and standard samples can be indexed into the sample sucking position and the bar code reading position for a short time period, and therefore the emergency and standard samples can be processed speedily.

What is claimed is:

1. An apparatus for delivering automatically routine samples contained in routine sample vessels and special samples such as emergency samples and standard samples contained in special sample vessels to be analyzed by an automatic chemical analyzer, comprising:
   a plurality of routine sample holding devices each holding a plurality of routine sample vessels;
   a first driving device for driving the routine sample holding devices so as to feed the routine sample vessels along a first path;
   a common sample holding device having a plurality of positions for holding special sample vessels and a plurality of positions for supporting said routine sample holding devices;

a second driving device for driving said common sample holding device so as to feed the special sample vessels along a second path which is arranged substantially at the same level as said first path and includes a portion substantially coincident with a portion of said first path at least at a sample sucking position; and a sample sucking device including a sucking probe for sucking routine samples and special samples indexed into said sample sucking position;

wherein the routine sample holding devices are successively indexed into a sample delivery position by driving said second driving device, routine sample vessels held by a routine sample holding device indexed at the sample delivery position are successively indexed into the sample sucking position by driving said first driving device, and special samples held in the special sample holding positions on the common sample holding device are successively directly indexed into the sample sucking position by driving only said second driving device.

2. An apparatus according to claim 1, further comprising means for reading information provided on routine sample vessels and special sample vessels at a substantially identical information reading position.

3. An apparatus according to claim 2, further comprising means for reading information provided on the routine sample holding devices.

4. An apparatus according to claim 3, further comprising means for detecting information provided on the special sample vessels.

5. An apparatus according to claim 1, wherein each of said routine sample holding devices comprises a sub-turntable having a plurality of routine sample vessel holding positions arranged equidistantly along a first circle thereon, said common sample holding device comprises a main-turntable on which said sub-turntables are arranged equidistantly along a second circle, and said special sample holding positions are provided on said main-turntable at positions between successive sub-turntables along a third circle, whereby a first circle of a sub-turntable indexed at the sample delivery position is crossed with said third circle on the main-turntable substantially at the sample sucking position.

6. An apparatus according to claim 5, wherein said first driving means comprises shafts each secured to respective sub-turntables, gears each secured to respective shafts, a common gear which is engaged with a gear secured to a shaft of a sub-turntable which is indexed at the sample delivery position, and a motor secured to said common gear.

* * * * *